US010136920B2

(12) United States Patent
Fisher et al.

(10) Patent No.: US 10,136,920 B2
(45) Date of Patent: Nov. 27, 2018

(54) ADJUSTABLE CALCANEAL RESTRAINT SYSTEM

(71) Applicants: Jonathan Fisher, Sandpoint, ID (US); Andrew Lundquist, Edina, MN (US)

(72) Inventors: Jonathan Fisher, Sandpoint, ID (US); Andrew Lundquist, Edina, MN (US)

( * ) Notice: Subject to any disclaimer, the term of this patent is extended or adjusted under 35 U.S.C. 154(b) by 0 days.

(21) Appl. No.: 14/986,424

(22) Filed: Dec. 31, 2015

(65) Prior Publication Data

US 2017/0189068 A1   Jul. 6, 2017

(51) Int. Cl.
*A61B 17/64* (2006.01)
*A61B 17/66* (2006.01)

(52) U.S. Cl.
CPC ........ *A61B 17/6441* (2013.01); *A61B 17/645* (2013.01); *A61B 17/6458* (2013.01); *A61B 17/66* (2013.01)

(58) Field of Classification Search
CPC .............. A61B 17/6441; A61B 17/645; A61B 17/6458; A61B 17/66; A61B 17/56
See application file for complete search history.

(56) References Cited

U.S. PATENT DOCUMENTS

| | | | |
|---|---|---|---|
| 4,584,995 A | 4/1986 | Koeneman | |
| 2007/0123857 A1* | 5/2007 | Deffenbaugh | A61B 17/025 606/54 |
| 2007/0161984 A1* | 7/2007 | Cresina | A61B 17/6425 606/54 |

FOREIGN PATENT DOCUMENTS

WO   WO2010/030960   3/2010

OTHER PUBLICATIONS

Prior publication showing a depiction of prior device, author unknown, title unknown, date unknown.

* cited by examiner

*Primary Examiner* — Julianna N Harvey
(74) *Attorney, Agent, or Firm* — Wells St. John, P.S.

(57) ABSTRACT

Disclosed is an adjustable and partially removable calcaneal restraint system and treatment method in the context of a first phase of surgery wherein a transverse calcaneal pin is inserted through the calcaneus and the calcaneal restraint system is then installed pending the second surgery. An aspect of the calcaneal restraint system also provides a partially removable framework to allow better or unimpeded access to the desired site for the second surgery stage of the treatment.

5 Claims, 5 Drawing Sheets

ADJUSTABLE CALCANEAL RESTRAINT SYSTEM

CROSS REFERENCE TO RELATED APPLICATION

This application does not claim the benefit of any other patent application.

TECHNICAL FIELD

This invention pertains to an adjustable calcaneal restraint system for use in medical treatments.

BACKGROUND OF THE INVENTION

The calcaneus is the name of the bone in a person's foot which is more generally known as the heel bone. Fractures of the calcaneus generally represent approximately two percent (2%) of all bone fractures, and can range from mild to severe. In moderate to severe cases where pieces of the calcaneus have separated, surgery is normally required to attempt to restore the heel as close as possible to its original condition.

In most cases the calcaneal fractures are primarily compression fractures and the primary problems that physicians need to address in treatment arise from a loss of height and width of the calcaneus, with some displacement of the subtalar joint. The subtalar joint is the complex joint below the ankle.

The treatment generally involves a two phase surgical correction or procedure. The correction generally includes two phases because the initial injury causes soft tissue inflammation or swelling and the calcaneus bone or bone pieces are not located where desired and the site of the operation is not ready for the final surgery. The first phase of the treatment will typically involve the implant or insertion of a calcaneal pin transversely through the calcaneal such that a first end and a second end of the calcaneal pin protrude on opposite sides of the patient's foot. During the initial surgery an external fixation device is placed on the leg and foot and attached to the calcaneal pin to restore length and height to the calcaneus bone that may have been lost as a result of the injury (such as a compression fracture).

The external fixation device is typically fixed to the patient's leg by placing pins in the front of the tibia combined with a transverse calcaneal pin inserted or implanted through the calcaneus. Once the calcaneal pin is placed or transversely fixed in the calcaneal, the calcaneal pin may be manipulated to bring the fracture and calcaneal into the desired state or condition. This may involve manually pulling and/or otherwise manipulating the calcaneal pin to place the fracture and calcaneal in a desired position (such as to a position of anatomical reduction).

The prior art external fixation devices normally include "clips" or attachment mechanisms that attach to the first end and second end of the transversely inserted calcaneal pin and tightened on the top bottom and sides to hold the calcaneal pin and consequently the calcaneal in a desired corrected position. A known problem with setting or fixing the calcaneal in the desired corrected position is that it is a very subjective procedure and it is difficult to consistently locate or fix the calcaneal in the desired or optimal position.

It should be noted that setting or fixing the calcaneal into this initial fixed position is subjectively accomplished in contemplation of a second surgery to repair the calcaneal or pieces thereof—preferably as close to the pre-injury position as possible.

Once the first phase of treatment, i.e. the first surgery and initial fixation is completed and the patient is out of the operating room, there is currently no practical way to adjust the level of correction imparted on the calcaneal without performing an additional surgery. When there is not any way to adjust the correction imposed on the calcaneal after the first surgery but before the second surgery, the outcome or success from the second surgery may be limited by the subjective placement or fixation performed in the first surgery. The subjective and imprecise nature of the fixation of the calcaneal during the first surgery combined with the inability to make any changes leading up to the second surgery, can negatively affect the outcome of the treatment of the patient during the second surgery. Again the second surgery portion of the treatment is when the patient's heel is opened up and the restorative work to the calcaneal is being done.

While there have been prior types of external fixation devices, the prior devices have been very complex and difficult to use, such that they are rarely or not often used.

While the goal of fixing the calcaneal with the external fixation device in the first surgery is to fix the patient's calcaneal in the optimal position, this does not always occur. The second surgery phase of the treatment typically involves opening the patient's foot up in the position it was fixed in during the first surgery and then for example placing a plate and/or screws onto the calcaneal bone or bone pieces to hold the fracture in place (presumably in the same position it was fixed during the first surgery). It is therefore evident how important the original fixation of the calcaneal is during the first surgery, to the overall outcome for the patient.

The second surgery phase of the patient treatment is also complicated or impeded by physical presence of the framework fixing the calcaneal during the second surgery.

The lateral portion of the frame of current devices is directly in front of the surgical site where the patient's foot would typically be opened. This requires the surgeon to perform a complex surgery while working around a portion of the external fixation device. The prior art devices therefore impose an undesirable obstacle to the second surgery portion of the treatment, further complicating the treatment.

It is therefore an object of embodiments of this invention to provide a calcaneal fixation device which reduces or eliminates the problems associated with possibly fixing the calcaneal in a less than desired position for the optimal outcome for the patient treatment.

An advantage of embodiments of this invention is that it provides an adjustable calcaneal fixation device which allows adjustment or changes to the fixed position of the patient's calcaneal after the first surgery part of the treatment and leading up to the second surgery portion of the treatment. Embodiments of this adjustable calcaneal fixation device further may provide complete adjustability in all planes both in the operation room during the first surgery phase, and after the first surgery. The correction provided by embodiments of this invention are therefore very consistent and reproducible. It also allows the surgeon to make adjustment after the surgery, in any plane that is desired, at any time in the postoperative period.

Embodiments of this invention further provide for dynamic distraction (versus only providing for static distraction) while allowing the patients heel to be moved gradually back into place while fixed before the second surgery.

It is also an object of embodiments of this invention to provide a calcaneal fixation device which does not pose an obstruction to the surgeon's access to the patient's heel during the second surgery.

An advantage of embodiments of this invention is that it may provide an external fixation device in which the framework is only located on one side of the patient's calcaneal during the surgery. This may be provided by providing a framework which includes structure on both sides of the calcaneal with the structure on the surgery side being removable for the surgery; or by providing a framework which only includes structure on the non-surgical side of the patient's calcaneus.

Despite the longstanding and recognized need for external calcaneal fixation devices which provide solutions to one or more of the objects of this invention, none until this invention have heretofore been developed.

Other objects, features, and advantages of this invention will appear from the specification, claims, and accompanying drawings which form a part hereof. In carrying out the objects of this invention, it is to be understood that its essential features are susceptible to change in design and structural arrangement, with only one practical and preferred embodiment being illustrated in the accompanying drawings, as required.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

Many of the fastening, connection, manufacturing and other means and components utilized in this invention are widely known and used in the field of the invention described, and their exact nature or type is not necessary for an understanding and use of the invention by a person skilled in the art or science; therefore, they will not be discussed in significant detail. Furthermore, the various components shown or described herein for any specific application of this invention can be varied or altered as anticipated by this invention and the practice of a specific application or embodiment of any element may already be widely known or used in the art or by persons skilled in the art or science; therefore, each will not be discussed in significant detail.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

Figure 1:
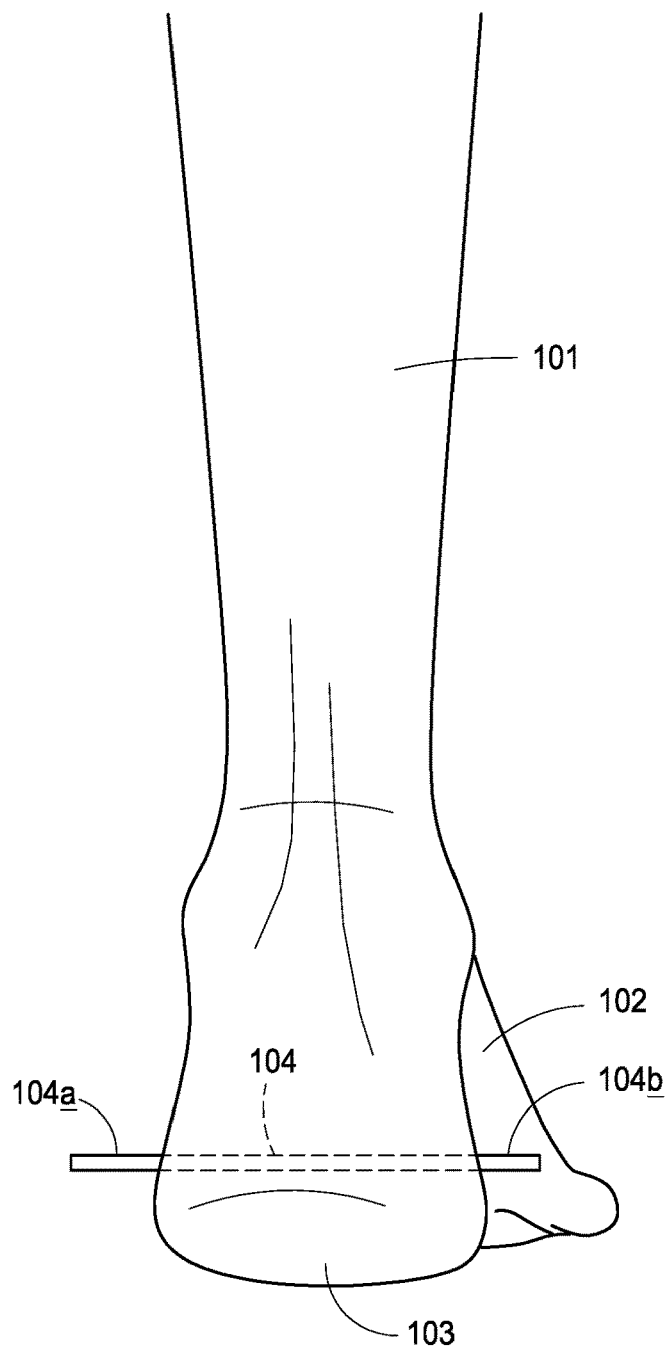
FIG. 1 is a rear view of a human foot and partial leg with a lateral or transverse calcaneal pin inserted therein.

FIG. 1 is a rear view of an exemplary partial human leg 101, foot 102 and heel portion 103 of the foot 102, illustrating a calcaneal pin 104 which has been surgically inserted or implanted transversely through the calcaneal bone (shown in later figures). The calcaneal pin 104 includes a first end 104a protruding on the "lateral" side or outside of the foot, and a second end 104b protruding on the medial side or inside of the foot.

In a first phase of treatment of an injured calcaneal, a calcaneal pin 104 is surgically inserted or implanted transversely through the calcaneal or heel bone, which then serves as a manipulation point or points for restraining or securing the calcaneus, as well as the manipulation thereof to achieve as desirable as possible of a position of the injured calcaneal (or pieces thereof) prior to the second phase of the treatment, namely the second surgery.

Figure 2:
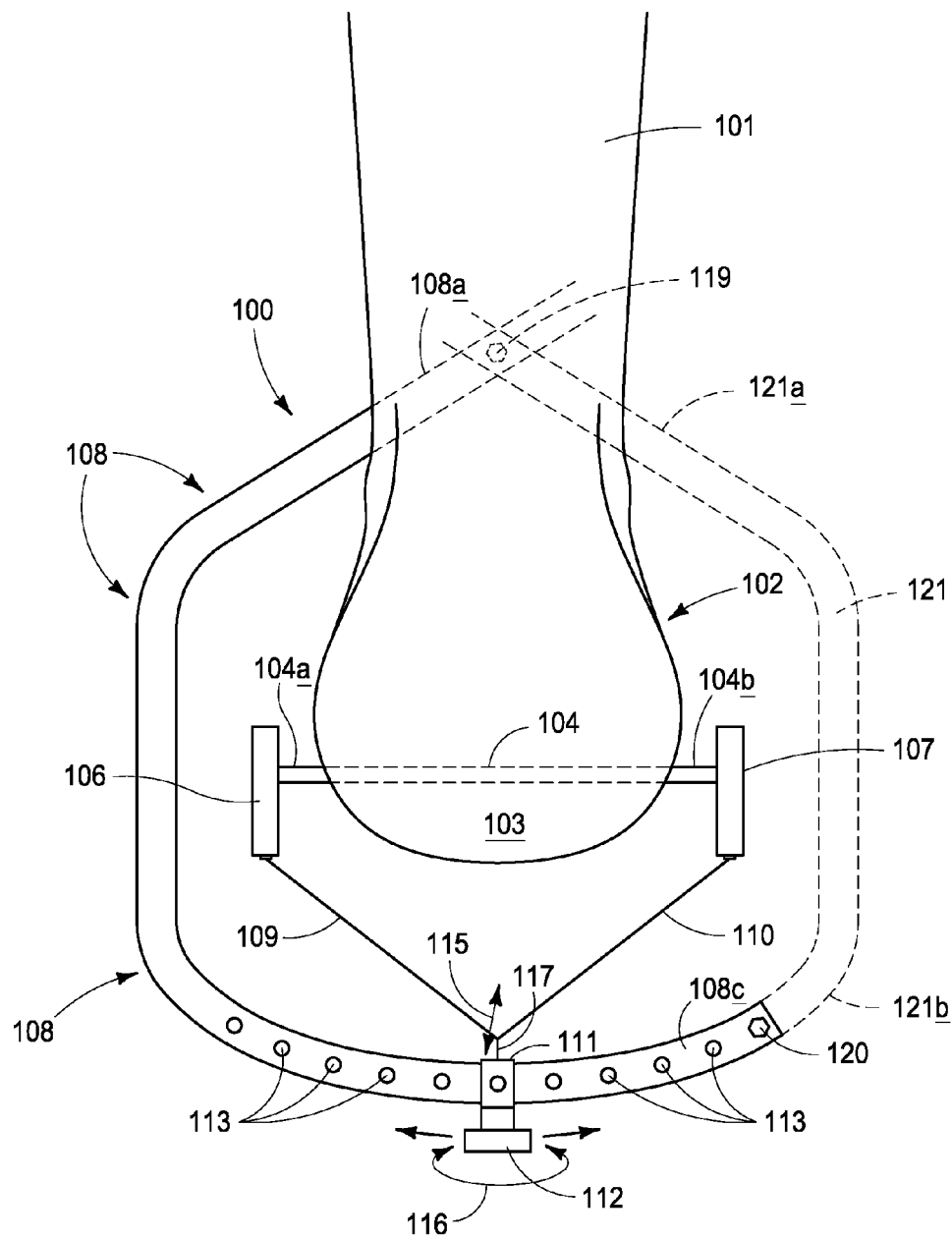
FIG. 2 is a rear view of a human foot and partial leg illustrating an example of one embodiment of a calcaneal restraint system contemplated by this invention attached thereto.

FIG. 2 is a rear elevation view of a leg 101 and foot 102 with one example of an embodiment of a calcaneal fixation system 100 contemplated by this invention, illustrating the first end 104a and the second end 104b of the calcaneal pin 104 each protruding laterally from the heel portion 103 of the foot 102.

The first cable or cable connector 109 and second cable or connector 110 are operably attached to the first end 104a and the second end 104b of the calcaneal pin 104 respectively through first attachment adapter 106 and second attachment adapter 107 respectively. While the first and second adapters 106 & 107 (which may be clips or latches) may be utilized to attach a first end of the first cable 109 and second cable 110 to the first end 104a and the second end 104b respectively of the calcaneal pin 104. The second end of the first cable 109 and of the second cable 110 are attached at a second end either directly to the framework cable adapter 111, or attached to an intermediate cable (which is in turn attached to the framework cable adapter 111). The first cable 109 and second cable 110 may also be attached together and both directly attached to the framework cable adapter 111, similar to a lasso.

In the example of the embodiment illustrated in FIG. 2, the framework cable adapter 111 is slidably mounted or attached to the calcaneal fixation framework 108. The calcaneal fixation framework 108 shown includes several cable adapter apertures 113 which provide a plurality of positions at which the framework cable adapter 111 may be positioned. The particular adapter aperture 113 chosen for a given patient or treatment procedure would be chosen by the treating physician based on the injury and desired goals of the treatment. What is important in some embodiments is that the framework cable adapter 111 can be adjusted (during the first surgery or thereafter) to seek to optimize the patient outcome.

Another aspect of the invention that may also be practiced is shown in FIG. 2, namely a tension biasing mechanism or adjustment positioning. FIG. 2 illustrates the second end of cables 109 and 110 attached to biasing cable 117. Biasing cable 117 may be elastic and initially set in tension so that a biasing force is imposed on the calcaneal pin 104 through first and second cables 109 and 110. Biasing or placing the patient's calcaneal in tension may be desirable to improve the position of the injured calcaneal for the second surgery portion of the treatment.

FIG. 2 further illustrates a rotatable threaded knob 112 on the framework cable adapter 111 which can be attached to cable 117 and to threaded knob 112 such that when the threaded knob 112 is rotated (arrow 116) it causes the knob 112 attached to the cable 117 to increase or decrease (arrow 115) the force imparted by first and second cables 109 and 110 on the calcaneal pin 104 (which may consequently alter or adjust the position of the injured portions of the patient's calcaneus).

FIG. 2 further illustrates an aspect of embodiments of this invention in which the calcaneal fixation system 100 has a removable framework portion 108a. The removable framework 121 section would be detachably secured to the fixed framework 108 at a first end 108a on a first end 121a, and to the lower portion 108c of the framework 108 at a second end 121b of the removable framework 121. The removable framework 121 can be attached or fixed to the permanent framework by any one of a number of different fastening means, with no one in particular being required to practice the invention. In the example shown in FIG. 2, a fastener 120 (a simple screw and nut configuration in this embodiment) configuration may be utilized. FIG. 2 further illustrates another fastener 119 (also a simple screw and nut configuration in this embodiment), for attaching and detaching the removable framework 121 at its first end 121a.

In practice the removable framework portion can be fixed to the patient's leg or preferably to the fixed part of the fixation framework 108 during or immediately after the first surgery and then removed just prior to or during the second surgery to provide the surgeon(s) performing the second surgery to operate without being impeded or impaired by a structure or framework.

Figure 3:
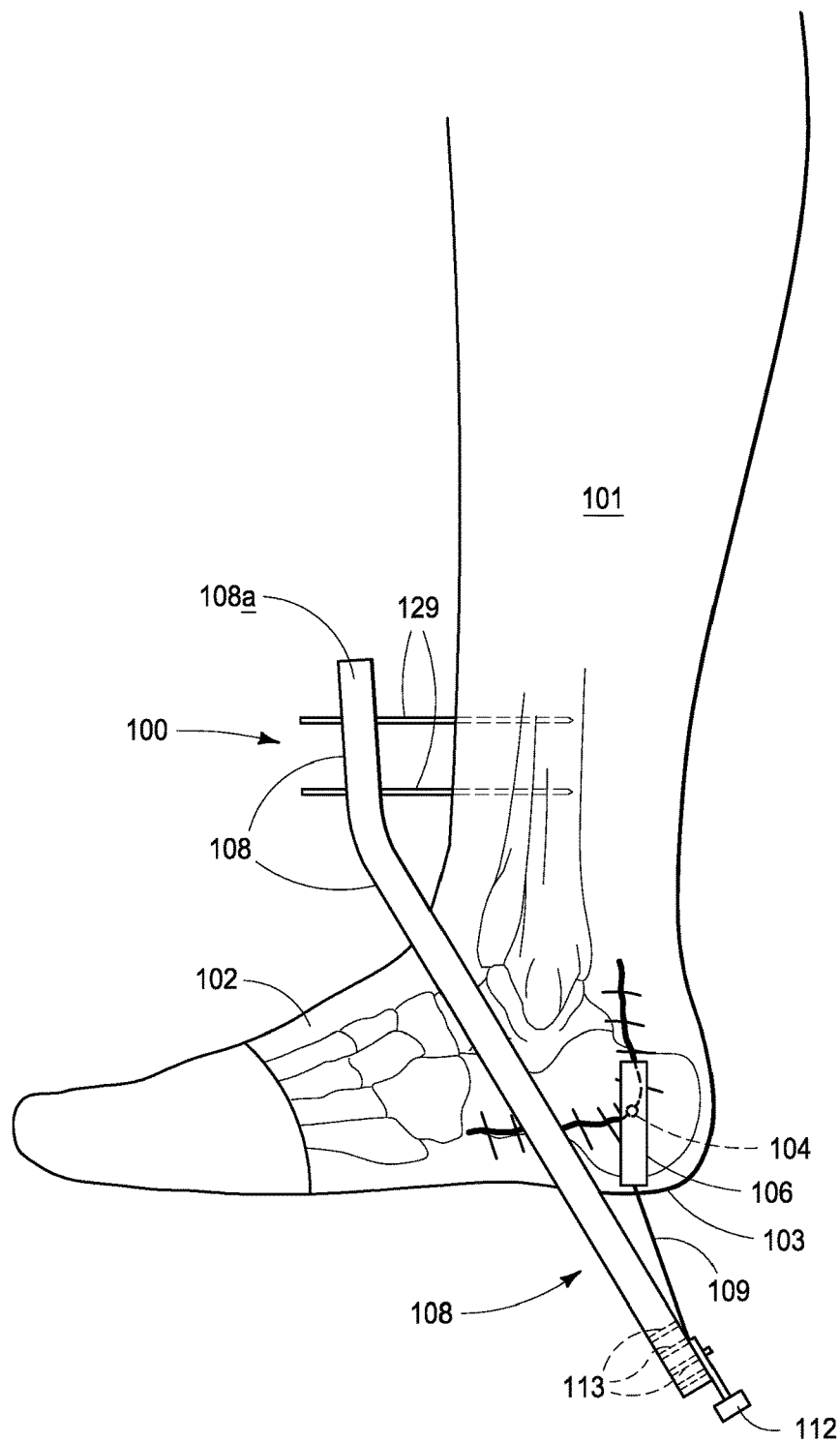
FIG. 3 is a side view of the example of the embodiment of the calcaneal restraint system shown in FIG. 2.

FIG. 3 is a side view of the example of the embodiment of the calcaneal restraint system shown in FIG. 2, illustrating a patient leg 101, foot 102, calcaneal fixation system 100, calcaneal pin 104 protruding laterally or transversely from the heel portion 103 of the foot 102. FIG. 3 further illustrates first connector 109 operably attached to the calcaneal pin 104 through first attachment adapter 106, first end 108a of fixed framework 108, and leg fasteners 129 which fix or secure the framework to the patient's leg, preferably the tibia bone. The leg fasteners may be any one of a number of different fasteners known in the industry, including without limitation, bone screws, nails, as well as threaded and smooth wires.

Figure 4:
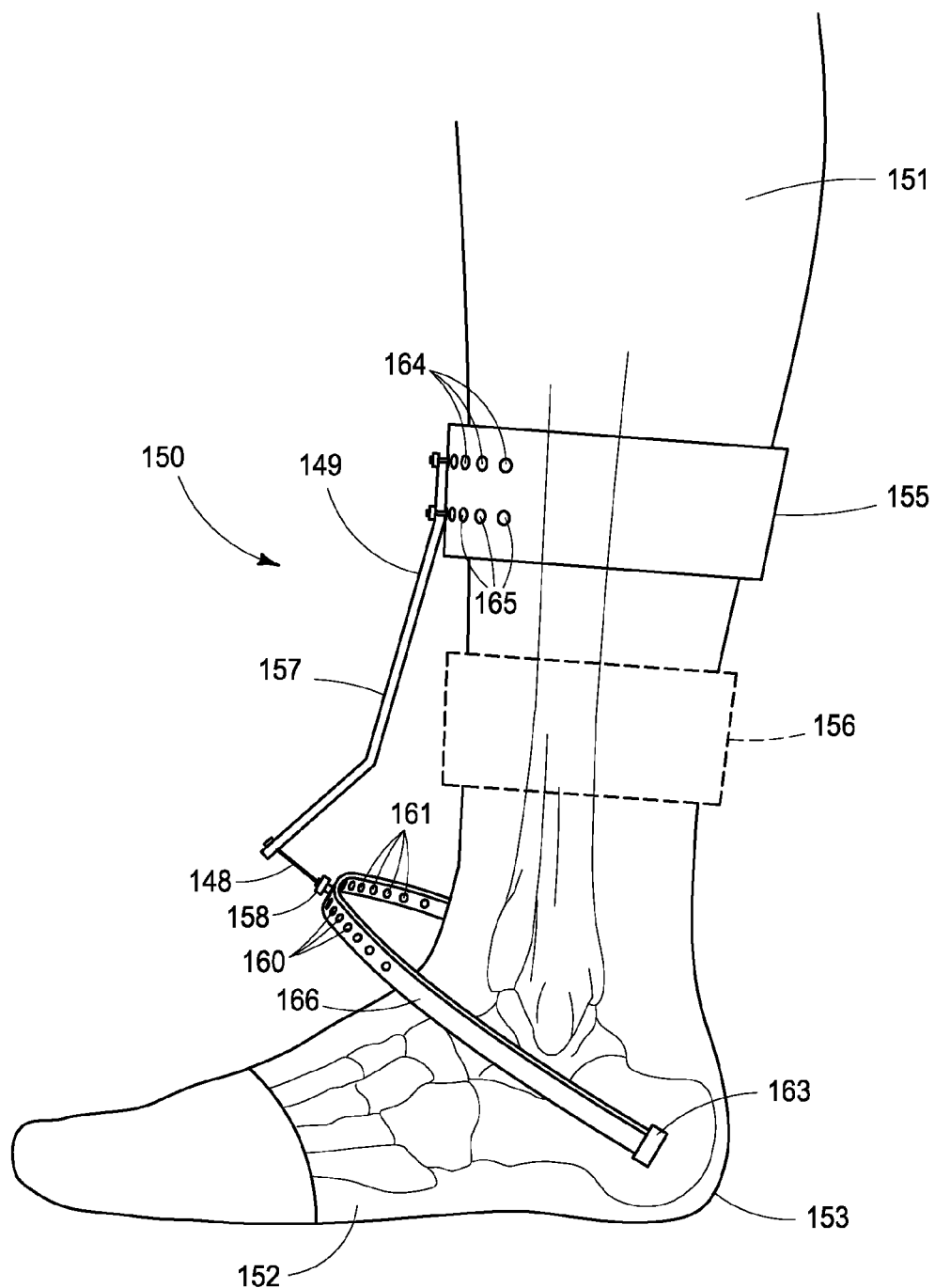
FIG. 4 is a side view of a human foot and partial leg, illustrating an example of another embodiment of a calcaneal restraint system contemplated by this invention attached thereto.

FIG. 4 is a side view of a human partial leg 151, a foot 152 and a heel portion 153 of the foot. FIG. 4 illustrates a different example of another embodiment of an adjustable calcaneal restraint system 150 contemplated by this invention attached thereto. FIG. 4 shows such an adjustable calcaneal restraint system 150 wherein the fixation framework 149 is securely attached to a patient's leg 151 via strap 155 and the location or angle at which the framework 149 is fixed may be adjusted by choosing different of the plurality of pairs of fastener apertures 164 and 165 on the strap 155 or a different fastener aperture of the fastener apertures 160 or 161.

The fixed framework 157 may be attached via cable 148 to the adjustable framework 166 by attaching it to any one of the plurality of fastener apertures 160 and 161 on either side of the adjustable framework 166.

Figure 5:
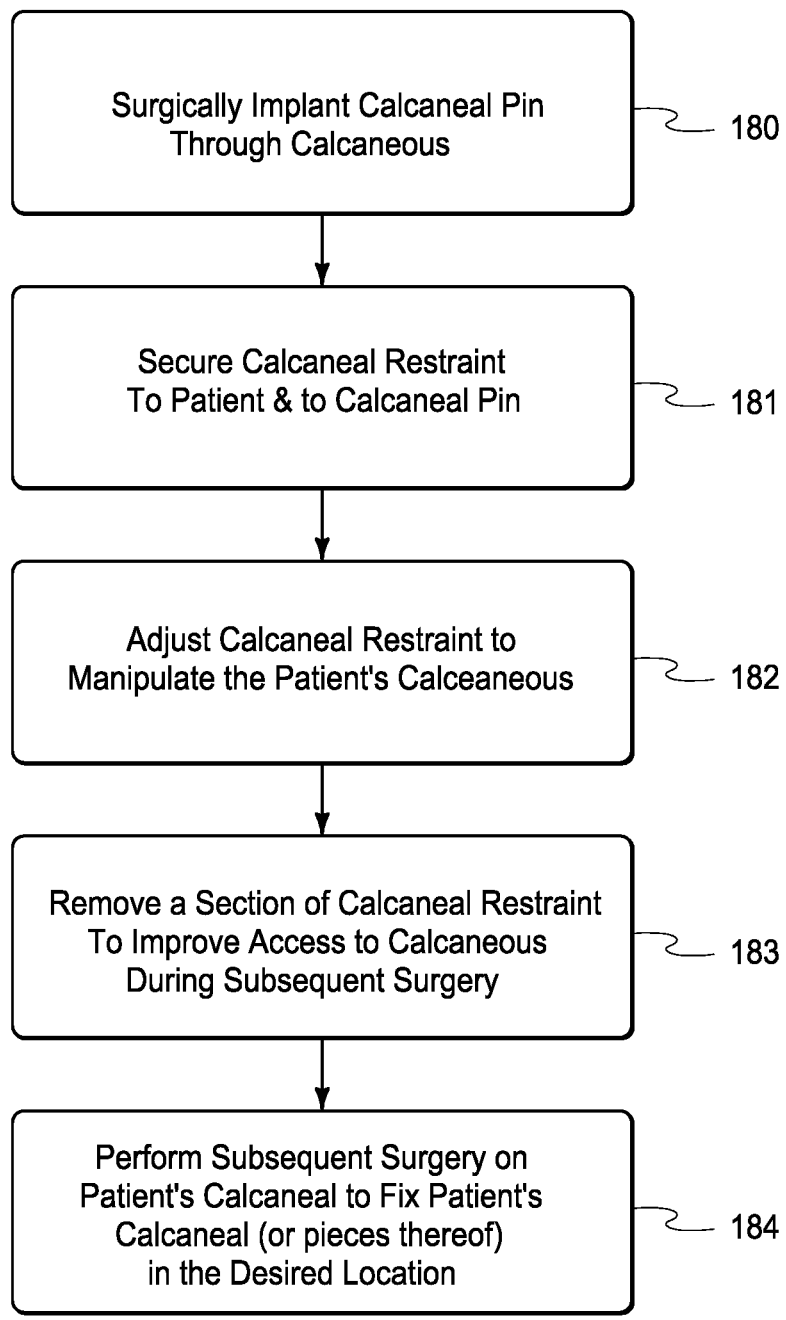
FIG. 5 is a flow chart illustrating an example of an embodiment of a method contemplated by this invention.

FIG. 5 is a flow chart illustrating an example of an embodiment of a treatment method contemplated by this invention. FIG. 5 generally illustrates step 180 wherein a first surgical procedure is performed and in which a calcaneal pin aperture is created laterally through a patient's calcaneal and a calcaneal pin is inserted transversely through the patient's calcaneus. Step 181 then involves providing an adjustable calcaneal restraint apparatus.

In embodiments of the invention the adjustable calcaneal restraint apparatus referred to in step 181 may comprise: a rigid framework with a first end configured to be affixed to a lower leg of the patient, and a second end configured for support transverse to the patient's heel; an adjustment member movably mounted to the second end of the rigid framework such that it can be set in transverse positions across the second end of the rigid framework; and wherein movement of the adjustment member relative to the second end of the rigid framework changes the calcaneus pin angle.

The adjustable calcaneal restraint apparatus secured to the patient as part of step 181, and adjusting the adjustable calcaneal restraint to manipulate the patient's calcaneus or pieces of the patient's calcaneus. The securing and the adjusting of the adjustable calcaneal restraint apparatus would typically be done during the first surgery.

In the embodiments of the invention wherein a part of the adjustable calcaneal restraint apparatus is removable, removing part of the rigid framework of the adjustable calcaneal restraint apparatus as part of step 183 to improve access to the calcaneus during the second surgery.

Step 184 then shows that a second surgery is performed on the patient's calcaneus to fix the calcaneus or pieces of the calcaneus in a desired location.

As will be appreciated by those of reasonable skill in the art, there are numerous embodiments to this invention, and variations of elements and components which may be used, all within the scope of this invention. In one embodiment for example, an adjustable calcaneal restraint apparatus for use in restraining a patient's foot including a calcaneus is provided, and comprises: a rigid framework with a first end configured to be affixed to a lower leg of the patient, and a second end configured for support transverse to the patient's heel; an adjustment member movably mounted to the second end of the rigid framework such that it can be set in transverse positions across the second end of the rigid framework; and wherein movement of the adjustment member relative to the second end of the rigid framework changes the calcaneus pin angle.

Further and/or additional embodiments to those disclosed in the preceding paragraph may be: further wherein the second end of the rigid framework is disposed for positioning below the patient's foot; further wherein the second end of the rigid framework is disposed for positioning above the patient's foot; further wherein the rigid framework is positioned on one lateral side of the patent's foot to provide lateral access to the patient's heel from the opposing side; further wherein a force bias member is attached to the rigid framework and configured such that the bias force is adjustable to either increase or decrease the bias force imposed on the calcaneus pin; further comprising an intermediate first calcaneus pin connector member attached to the first end of the calcaneus pin and a second calcaneus pin connector member attached to the second end of the calcaneus pin, with both the first and second calcaneus pin connector members attached to the adjustment member such that the adjustment member can provide adjustable angle to the calcaneus pin; further wherein the framework is affixed to the tibia of the lower leg by fasteners; and/or further wherein the framework is externally affixed around the lower leg of the patient.

Still further embodiments from those identified in the preceding paragraph, an adjustable calcaneal restraint apparatus may be provided further comprising a biasing member disposed between the calcaneus pin and the adjustment member or the second end of the framework to provide a bias force on the calcaneus pin; and still further wherein the biasing force imposed by the biasing member on the calcaneus pin is a tension or compression biasing force.

Still further embodiments from those identified in the preceding paragraph, an adjustable calcaneal restraint apparatus may be provided further wherein one of the medial member and the lateral member are disposed for removal to facilitate increased access to the patient's heel; and/or still further wherein both the medial member and the lateral member are disposed for independent removal to facilitate increased access to the patient's heel.

It should also be noted that embodiments of this invention provide a treatment method for treating injuries to a patient's calcaneus performing a first surgical procedure wherein a calcaneal pin aperture is created laterally through a patient's calcaneal; inserting a calcaneal pin transversely through the patient's calcaneal; providing an adjustable calcaneal restraint apparatus, the adjustable calcaneal restraint apparatus comprising: a rigid framework with a first end configured to be affixed to a lower leg of the patient, and a second end configured for support transverse to the patient's heel; an adjustment member movably mounted to the second end of the rigid framework such that it can be set in transverse positions across the second end of the rigid framework; and wherein movement of the adjustment member relative to the second end of the rigid framework changes the calcaneus pin angle; securing the adjustable calcaneal restraint apparatus to the patient; adjusting the adjustable calcaneal restraint to manipulate the patient's calcaneus or pieces of the patient's calcaneus; and performing a second surgical procedure on the patient's calcaneus to fix the calcaneus or pieces of the calcaneus in a desired location.

Further and/or additional embodiments to those disclosed in the preceding paragraph may be a treatment method for treating injuries to a patient's calcaneus and: further wherein before the second surgical procedure is performed, a portion of the rigid framework is removed to provide better access to a surgical location and/or further wherein the securing of the adjustable calcaneus restraint apparatus to the patient is securely fastening the first end of the structure to a bone of the patient.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A treatment method for treating injuries to a patient's calcaneus performing a first surgical procedure wherein a calcaneal pin aperture is created laterally through a patient's calcaneus;
   inserting a calcaneal pin transversely through the patient's calcaneus;
   providing an adjustable calcaneal restraint apparatus, the adjustable calcaneal restraint apparatus comprising:
      a rigid framework with a first end configured to be affixed to a lower leg of the patient, and a second end configured for support transverse to the patient's heel;
      an adjustment member operably connected to a first end and a second end of the calcaneal pin by a cable, the adjustment member being movably mounted to the second end of the rigid framework such that it can be set in transverse positions across the second end of the rigid framework; and
      wherein movement of the adjustment member relative to the second end of the rigid framework changes the calcaneus pin angle;
   securing the adjustable calcaneal restraint apparatus to the patient;
   adjusting the adjustable calcaneal restraint apparatus to manipulate the patient's calcaneus or pieces of the patient's calcaneus;
   imparting a biasing force on the cable between the adjustment member and the calcaneal pin;
   waiting an amount of time for the patient's calcaneal and surrounding tissue to be in a desirable condition to perform a second surgical procedure; and
   performing the second surgical procedure on the patient's calcaneus to fix the calcaneus or pieces of the calcaneus in a desired location while the adjustable calcaneal restraint apparatus is fixed to the patient.

2. A treatment method for treating injuries to a patient's calcaneus as recited in claim 1, and wherein before the second surgical procedure is performed, a portion of the rigid framework is removed to provide better access to a surgical location.

3. A treatment method for treating injuries to a patient's calcaneus as recited in claim 1, and wherein the securing of the adjustable calcaneus restraint apparatus to the patient is securely fastening the first end of the rigid framework to a bone of the patient.

4. A treatment method for treating injuries to a patient's calcaneus as recited in claim 1, and further wherein the biasing force imparted on the cable between the adjustment member and the calcaneal pin places the patient's calcaneus in tension.

5. A treatment method for treating injuries to a patient's calcaneus as recited in claim 1, and further wherein the rigid framework includes a removable framework portion detachably secured to the rigid framework; and removing detaching the removable framework portion to provide improved access to the patent's heel during the second surgery.

* * * * *